US005674499A

United States Patent [19]

Willemse et al.

[11] Patent Number: 5,674,499

[45] Date of Patent: Oct. 7, 1997

[54] EQUINE HERPESVIRUS GENE 15 MUTANTS

[75] Inventors: Martha Jacoba Willemse, Nijmegen; Paulus Jacobus Antonius Sondermeijer, Boxmeer, both of Netherlands; Lesley Nicolson, Glasgow, Scotland

[73] Assignee: Akzo Nobel N.V., Arnhem, Netherlands

[21] Appl. No.: 360,103

[22] Filed: Dec. 20, 1994

[30] Foreign Application Priority Data

Dec. 20, 1993 [EP] European Pat. Off. .............. 93203584

[51] Int. Cl.$^6$ ........................ A61K 39/27; A61K 39/295; C12N 7/00; C12N 5/10

[52] U.S. Cl. ...................................... 424/199.1; 424/205.1; 424/229.1; 435/235.1; 435/172.3; 435/320.1; 435/252.3; 435/325; 536/23.72

[58] Field of Search ................................ 435/69.3, 235.1, 435/240.2, 172.3, 320.1, 252.3, 325; 424/199.1, 205.1, 229.1, 820; 536/23.72

[56] References Cited

FOREIGN PATENT DOCUMENTS

WOA 92 01045 1/1992 European Pat. Off. .

OTHER PUBLICATIONS

Matsumura et al., "DNA sequence and transcriptional analyses of the region of the Equine Herpesvirus type 1 Kentucky A strain genome encoding glycoprotein C," *Virology*, 193:2, Apr. 1993, pp. 910–923.

Nicolson et al., "The nucleotide sequence of the Equine Herpesvirus 4 gC gene homologue, " *Virology*, 179:2, Nov. 1990, pp. 378–387.

Telford et al. Virology 189:304–316, 1992.

Ostlund et al. Vet. Clin North Am Equine Pract Aug. 1993 vol. 9 (2): 283–294.

*Primary Examiner*—Mary E. Mosher
*Assistant Examiner*—Ali R. Salimi
*Attorney, Agent, or Firm*—Mary E. Gormley

[57] ABSTRACT

The present invention relates to an Equine herpesvirus (EHV) vaccine comprising an EHV having an insertion or deletion in the gene 15 of the EHV genome.

16 Claims, 3 Drawing Sheets

EQUINE HERPESVIRUS GENE 15 MUTANTS

FIELD OF THE INVENTION

The present invention is concerned with an Equine herpesvirus mutant, a recombinant DNA molecule comprising an Equine herpesvirus nucleic acid sequence, a host cell transfected with said recombinant DNA molecule or infected with the Equine herpesvirus mutant, as well as vaccine comprising such an Equine herpesvirus mutant.

BACKGROUND OF THE INVENTION

Equine herpesviruses (EHV) comprise a group of antigenically distinct biological agents which cause a variety of infections in horses ranging from subclinical to fatal disease.

Equine herpesvirus-1 (EHV-1) is a ubiquitous pathogen in horses of major economic importance associated with epidemics of abortion, respiratory tract disease, and central nervous system disorders. Primary infection of upper respiratory tract of young horses results in a febrile illness which lasts for 8 to 10 days. Immunologically experienced mares may be reinfected via the respiratory tract without disease becoming apparent, so that abortion usually occurs without warning. The neurological syndrome is associated with respiratory disease or abortion and can affect animals of either sex at any age, leading to incoordination, weakness and posterior paralysis (Telford, E. A. R. et al., Virology 189, 304–316, 1992).

EHV-2, or equine cytomegalovirus, is a ubiquitous, antigenically heterogeneous, usually slowly growing group of viruses, causing no known disease.

EHV-3, equine coital exanthema virus, is the causative agent of a relatively mild progenital exanthema of both mare and stallion.

EHV-4, previously classified as EHV-1 subtype 2, is primarily associated with respiratory disease although sporadic EHV-4 induced abortions have been reported.

The genomic structure of the EHVs is similar to that of other alpha herpesviruses comprising a double-stranded linear DNA molecule consisting of two covalently linked segments ($U_L$ and $U_S$), the $U_S$ segment being flanked by inverted repeats.

The characterization of the EHV-1 genome has been reported by Whalley, J. M. et al. (J. Gen. Virol. 57, 307–323, 1981), whereas that of the EHV-4 genome is disclosed by Cullinane, A. A. et al. (J. Gen. Virol. 69, 1575–1590, 1988).

The majority of studies on the molecular biology of EHV have concerned EHV-1. Recently, the complete DNA sequence of EHV-1 was presented by Telford et al., 1992 (supra). It was found that the genome consists of about 150,000 bp and 76 distinct genes have been recognized up to now. These genes have been mapped exactly on the EHV-1 genome and the relationship of these genes with the corresponding HSV-1 analogues are determined therein. This includes gene 15 which is mapped in the $U_L$ segment of the EHV-1 genome, collinear with its HSV-1 analogue $U_L$45. Previously, several genes encoding (glyco)proteins of EHV-1 have been mapped, e.g. gB (Whalley, J. M. et al., J. Gen. Virol. 79, 383–394), gC (Allen, G. P. et al., J. Gen. Virol. 62, 2850–2858, 1988), gD, gI, gE (Audonnet, J. C. et al., J. Gen. Virol. 71, 2969–2978,1990), gH (Robertson, G. R. et al., DNA Sequence 1, 241–249, 1991) and TK (Robertson, G. R. et al., Nucleic Acid Res. 16, 11303–11317, 1988).

The map positions and nucleotide sequences of several genes encoding (glyco)proteins of EHV-4 have also been determined, e.g. gH and gB (Nicolson, L. et al., J. Gen. Virol. 71, 1793–1800, 1990), gE (Cullinane, A. et al., 1988, supra), TK (PCT-application WO 92/01045), and gC (Nicolson, L. et al., Virology 179, 378–387, 1990) the latter also disclosing the nucleotide sequence of the EHV-1 gene 15 analogue.

It has further been demonstrated that the EHV-1 and EHV-4 genes are closely collinear with each other as well as with their HSV-1 counterparts (Telford et al., 1992, supra; Cullinane et al., 1988, supra) indicating that a certain gene in a specific virus has a positional counterpart in the other herpesviruses.

Control of EHV infection by means of vaccination has been a long-sought goal. Current vaccines against these viruses comprise chemically inactivated viruses or attenuated live viruses which require multiple administration and have limited efficacy.

Inactivated vaccines generally induce only a low level of immunity, requiring additional immunizations, disadvantageously require adjuvants and are expensive to produce. Further, some infectious virus particles may survive the inactivation process and cause disease after administration to the animal.

In general, attenuated live virus vaccines are preferred because they evoke a more long-lasting immune response (often both humoral and cellular) and are easier to produce.

Up to now only live, attenuated Equine herpes-virus vaccines were available which are based on live Equine herpesviruses attenuated by serial passages of virulent strains in tissue culture. However, because of this treatment uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals. Furthermore, with the existing live attenuated Equine herpesvirus vaccines a positive serological test is obtained for Equine herpesvirus infection. Thus, with the existing Equine herpesvirus vaccines, it is not possible to determine by a serological test, e.g. an Elisa, whether a specific animal is a latent carrier of the virulent virus or is vaccinated.

Furthermore, it would be advantageous if an Equine herpesvirus strain could be used as a vaccine that affords protection against both Equine herpes-virus infection and an other equine pathogen. This could be achieved by inserting a gene encoding a relevant antigen of the equine pathogen into the genome of the Equine herpesvirus in such a way that upon replication of the Equine herpesvirus both Equine herpesvirus antigens and the antigen of the other equine pathogen are expressed.

SUMMARY OF THE INVENTION

The present invention provides an EHV mutant comprising a mutation in the EHV genome in a region spanning gene 15 of EHV.

A mutation is understood to be a change of the genetic information in the above-mentioned region with respect to the genetic information present in this region of the genome of naturally occurring EHV.

The mutation is, for example, a nucleic acid substitution, deletion, insertion or inversion, or a combination thereof resulting in an EHV mutant which fails to produce any antigenic or functional polypeptide encoded by the EHV gene 15.

Figure 1:
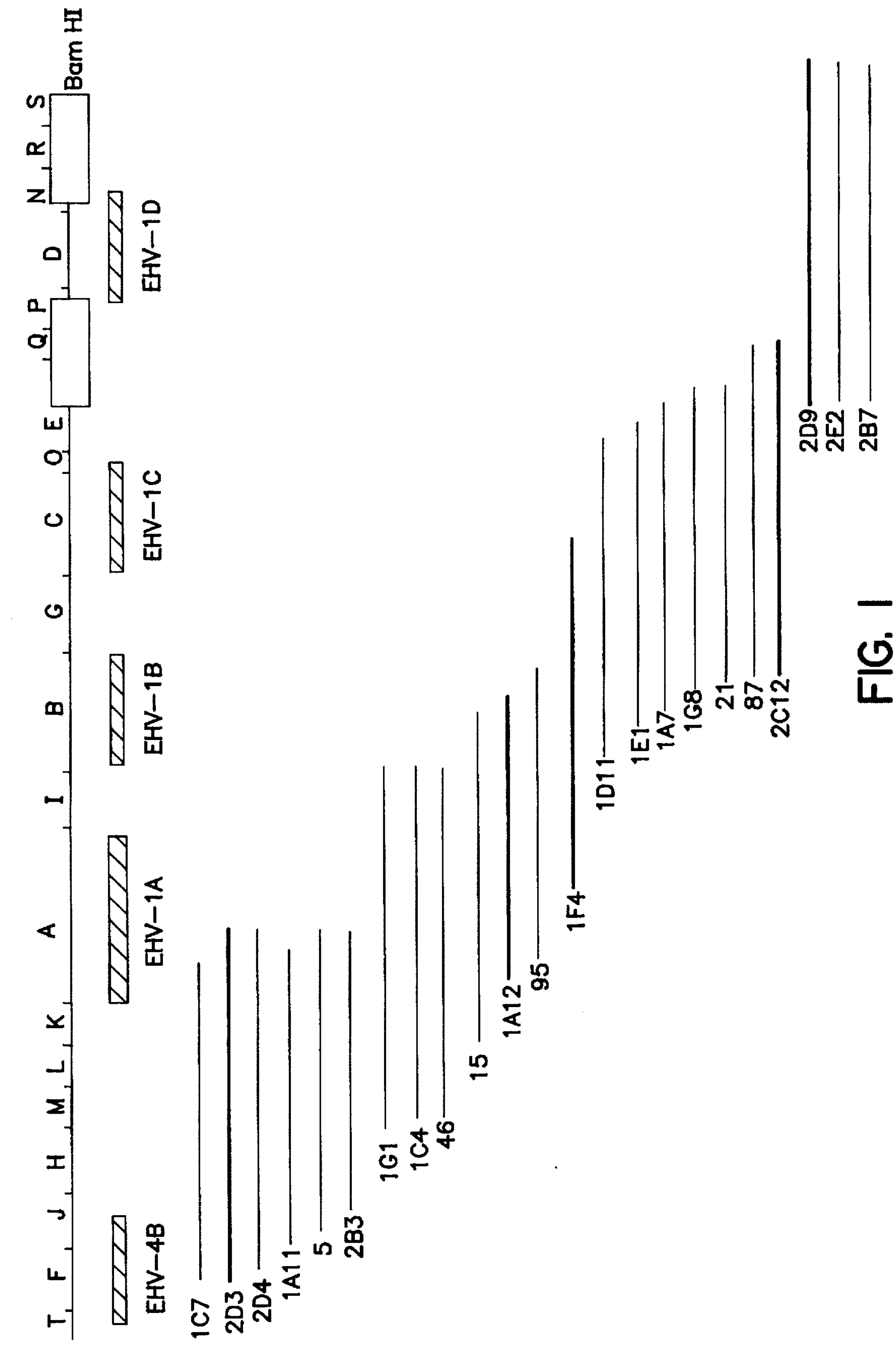
FIG. 1 is a summary of all generated overlapping cosmids containing the indicated fragment of the EHV-1 genome. The upper line represents the BamHI restriction enzyme map of the EHV-1 genome.

Preferably, the mutation introduced into the defined region of the EHV genome is a deletion of whole or part of the EHV gene 15, and/or an insertion of a heterologous nucleic acid sequence therein.

In particular the present invention provides an insertion EHV mutant characterized in that it comprises a heterologous nucleic acid sequence, said nucleic acid sequence being introduced in the region of the EHV genome spanning the gene 15 of EHV.

The EHV mutant according to the present invention can be derived from any available EHV strain, e.g. strain M8, Ab4, Kentucky D or T431 and 1942.

The term "insertion EHV mutant" as used herein denotes infective virus which has been genetically modified by incorporation into the virus genome of a heterologous nucleic acid sequence, i.e. DNA which comprises a nucleic acid sequence not present in the EHV gene 15 naturally found in EHV.

On infection of a cell by the insertion EHV mutant, it may express the heterologous gene in the form of a heterologous polypeptide.

The term "polypeptide" refers to a molecular chain of amino acids, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

DETAILED DESCRIPTION OF THE INVENTION

The prerequisite for a useful EHV mutant is that the mutation such as an inserted heterologous nucleic acid sequence is incorporated in a permissive position or region of the EHV genome, i.e. a position or region which can be used for the incorporation of the mutation without disrupting essential functions of EHV such as those necessary for infection or replication.

The region referred to in the present invention for incorporation of the mutation, i.e. gene 15 of EHV has not been identified previously as a non-essential region. Surprisingly, it has been found that a mutation such as the insertion of a heterologous nucleic acid sequence or deletion of (part of) this region is allowable without disrupting essential functions of EHV.

Unexpectedly, it has been found that the introduction of a mutation into the region defined above reduces the virulence of the live EHV mutant without affecting the protective properties of the EHV mutant. This finding offers the possibility to obtain an attenuated EHV mutant, e.g. by introducing a deletion or insertion into said region, which mutant can be administered to the animals to be vaccinated in a live form.

The term "gene 15 of EHV" is used herein to identify the open reading frame (ORF) which is present in the EHV genome 3' adjacent the gene encoding the glycoprotein C homologue (gC) including also the 5' flanking intergenic sequence of the ORF of gene 15, i.e. the nucleotide sequence between the gene encoding the gC homologue and gene 15, irrespective of the type of EHV.

The exact position of the gene encoding the gC homologue of EHV-1 has been mapped (on the BamHI H fragment) and sequenced by Allen et al., 1988 (supra). Similar information is available for EHV-4 from Nicolson et al., 1990 (supra).

Gene 15 of EHV-1 and EHV-4 have been identified by Telford et al., 1992 (supra) and Nicolson et al., 1990 (supra), respectively. However, it appeared that no sequence homology exists between gene 15 of EHV and genes having positional counterparts in HSV-1 or VZV.

The ORF of gene 15 of EHV-1 spans base pairs 21170 (start)-20487 (stop) (Telford et al., 1992, supra) and encodes a polypeptide having 227 amino acids (the DNA sequence and amino acid sequence are shown in SEQ ID NO: 1 and 2).

The ORF of gene 15 of EHV-4 spans base pairs 2110 (start)-2790 (stop) (Nicolson et al., 1990, supra) and encodes a polypeptide having 226 amino acids (the DNA sequence and amino acid sequence are shown in SEQ ID NO: 3 and 4).

In a preferred embodiment of the present invention the EHV mutant is an EHV-1 having a mutation in a region spanning the ORF of gene 15 encoding a polypeptide having an amino acid sequence shown in SEQ ID NO: 2, or is an EHV-4 having a mutation in a region spanning the ORF of gene 15 encoding a polypeptide having an amino acid sequence shown in SEQ ID NO: 4.

In particular, said regions have a nucleotide sequence as shown in SEQ ID NO: i (EHV-1) or SEQ ID NO: 3 (EHV-4), respectively.

It will be understood that for the DNA sequence of either of the EHV genomes, natural variations can exist between individual EHV viruses. These variations may result in deletions, substitutions, insertions, inversions or additions of one or more nucleotides.

These EHV variants may encode a corresponding gene 15 that differs from the gene 15 sequences specifically disclosed herein. The DNA sequence encoding such variant ORFs can be located by several methods, including hybridization with the DNA sequence provided in SEQ ID NO: 1 and 3 or comparison of the physical map to locate analogous regions encoding said gene. Therefore, the present invention provides a region for introducing a mutation obtainable from any strain of EHV.

Moreover, the potential exists to use genetic engineering technology to bring about the above-mentioned variations resulting in a DNA sequence related to the DNA sequence of the region defined above. It is clear that an EHV mutant comprising a mutation incorporated into a region located within the EHV genome characterized by such a related DNA sequence is also included within the scope of the present invention.

Furthermore, as the region defined above does not display essential functions of the virus, said region can be deleted partially or completely, whereafter a heterologous nucleic acid sequence can be incorporated into said deletion if desired.

The heterologous nucleic acid sequence to be inserted into the EHV genome for the insertional inactivation of the gene 15 can be derived from any source, e.g. viral, prokaryotic, eukaryotic or synthetic.

In a particular embodiment of the invention said inserted heterologous nucleic acid sequence is a non-coding oligonucleotide, the length and sequence of which are not critical, but preferably varies between 8–100 nucleotides in length.

A very suitable non-coding oligonucleotide comprises translational stop codons in each of the possible reading frames in both directions, in addition to appropriate, e.g. unique, restriction enzyme cleavage sites.

It is a further object of the present invention to provide a mutant Equine herpesvirus which can be used not only for the preparation of a vaccine against Equine herpesvirus infection but also against other equine infectious diseases. Such a vector vaccine based on a safe live attenuated Equine herpesvirus mutant offers the possibility to immunize against other pathogens by the expression of antigens of said pathogens within infected cells of the immunized host and can be obtained by inserting a heterologous nucleic acid sequence encoding a polypeptide heterologous to the specific Equine herpesvirus in the region of the Equine herpesvirus genome defined herein.

Said heterologous nucleic acid sequence may encode an antigen of an equine pathogen such as equine influenza virus, -rotavirus, -infectious anemia virus, arteritis virus, -encephalitis virus, Borna disease virus of horses, Berne virus of horses, *E. coli* or *Streptococcus equi.*

Heterologous means that it is also possible that a specific type of EHV, e.g. EHV-1, is used as a vector virus for the incorporation of a nucleic acid sequence encoding an antigen of another type of EHV, e.g. EHV-4 or vice versa.

An essential requirement for the expression of the heterologous nucleic acid sequence by an EHV mutant is an adequate promotor operably linked to the heterologous nucleic acid sequence.

It is obvious to those skilled in the art that the choice of a promotor extends to any eukaryotic, prokaryotic or viral promotor capable of directing gene transcription in cells infected by the EHV mutant, e.g. promotors of the retroviral long terminal repeat (Gorman et al., Proc. Natl. Acad. Sci. USA 79, 6777–6781, 1982), the SV40 promotor (Mulligan and Berg, Science 209, 1422–1427, 1980) or the cytomegalovirus immediate early promotor (Schaffner et al., Cell 41, 521–530, 1985).

Well-known procedures for inserting DNA sequences into a cloning vector and in vivo homologous recombination or cosmid cloning techniques can be used to introduce a mutation into the Equine herpesvirus genome (Maniatis, T. et al. (1982) in "Molecular cloning", Cold Spring Harbor Laboratory; European Patent Application 74.808; Roizman, B. and Jenkins, F. J. (1985), Science 229, 1208; Higuchi, R. et al. (1988), Nucleic Acids Res. 16, 7351).

Briefly, this can be accomplished by constructing a recombinant DNA molecule for recombination with Equine herpesvirus DNA. Such a recombinant DNA molecule comprises vector DNA which may be derived from any suitable plasmid, cosmid, virus or phage, and contains Equine herpesvirus DNA of the region identified above.

Examples of suitable cloning vectors are plasmid vectors such as pBR322, the various pUC and Bluescript plasmids, cosmid vectors, e.g. THV, pJB8, MUA-3 and CosI, bacteriophages, e.g. lambda-gt-WES-lambda B, charon 28 and the M13mp phages or viral vectors such as SV40, Bovine papillomavirus, Polyoma and Adeno viruses. Vectors to be used in the present invention are further outlined in the art, e.g. Rodriguez, R. L. and D. T. Denhardt, edit., Vectors: A survey of molecular cloning vectors and their uses, Butterworths, 1988.

A deletion to be introduced in the described region can be incorporated first in a recombinant DNA molecule carrying the gene 15 of EHV by means of a restriction enzyme digest with one or more enzymes of which the cleavage sites are correctly positioned in or near the open reading frame of gene 15. Recircularization of the remaining recombinant DNA molecule would result in a derivative lacking at least part of the coding sequence present within the identified region. Alternatively, progressive deletions can be introduced either in one or two directions starting from within a restriction enzyme cleavage site present within the sequence of the gene 15. Enzymes such as Bali, Bal31 or exonuclease III can be used for this purpose. Recircularized molecules are transformed into *E. coli* cells and individual colonies can be analyzed by restriction mapping in order to determine the size of the deletion introduced into the specified region. An accurate positioning of the deletion can be obtained by sequence analysis.

In case the insertion of a heterologous nucleic acid sequence is desired the recombinant DNA molecule comprising the EHV gene 15 may be digested with appropriate restriction enzymes to produce linear molecules whereafter the heterologous nucleic acid sequence, if desired linked to a promoter, can be ligated to the linear molecules followed by recircularization of the recombinant DNA molecule.

Optionally, a deletion is introduced into the EHV gene 15 concomitantly with the insertion of the heterologous nucleic acid sequence.

Appropriate restriction enzymes to be used for cleaving the EHV 15 gene are for example ScaI (EHV-1) and BglII, NarI or XbaI (EHV-4).

In case the method of in vivo homologous recombination is applied for the preparation of an EHV mutant according to the invention the EHV sequences which flank the deleted gene 15 sequences or the inserted heterologous nucleic acid sequences should be of appropriate length, e.g. 50–3000 bp, as to allow in vivo homologous recombination with the viral EHV genome to occur.

Subsequently, cells, for example equine cells such as equine dermal cells (NBL-6) or cells from other species such as RK13, Vero and BHK cells can be transfected with EHV DNA in the presence of the recombinant DNA molecule containing the mutation flanked by appropriate EHV sequences whereby recombination occurs between the EHV sequences in the recombinant DNA molecule and the corresponding sequences in the EHV genome.

Recombinant viral progeny is thereafter produced in cell culture and can be selected for example genotypically or phenotypically, e.g. by hybridization, detecting enzyme activity encoded by a gene co-integrated along with the heterologous nucleic acid sequence or detecting the antigenic heterologous polypeptide expressed by the recombinant EHV immunologically. Recombinant virus can also be selected positively based on resistance to compounds such as neomycin, gentamycin or mycophenolic acid. The selected EHV mutant can be cultured on a large scale in cell culture whereafter EHV mutant containing material or heterologous polypeptides expressed by said EHV can be collected therefrom.

Alternatively, the EHV mutant according to this invention can also be produced by co-transfection of a cosmid set (de Wind, N. et al., J. Gen. Virol 64, 4691–4696, 1990) containing overlapping fragments comprising the entire EHV genome, wherein one of the cosmids comprises a fragment of the EHV genome comprising the mutated gene 15.

A very suited cosmid set which can be used to produce an EHV mutant according to the invention is disclosed in Example 1. The EHV-1 gene 15 is positioned within the EHV-1 insert cloned in cosmid 2D3 spanning bp. 1-42750 (numbering derived from Telford et al., 1992, supra).

In a further preferred embodiment the invention provides an EHV mutant as described above said mutant additionally comprising a mutation, if desired an attenuating mutation, in particular a deletion or insertion, in another gene of the EHV genome.

This mutation may result in the inactivation of a gene such that said gene is not able to express a functional polypeptide anymore resulting in an EHV mutant with reduced virulence. This can be achieved by introducing a mutation in for example the gene encoding gE, TK, RR or $U_L21$ (Telford et al., 1992, supra; Robertson et al., 1988, supra; WO 92/01045).

A live EHV mutant according to the present invention, and in particular a live EHV mutant expressing one or more different heterologous polypeptides of specific equine pathogens, can be used to vaccinate horses. Vaccination with such a live vector vaccine is preferably followed by replication of the EHV mutant the inoculated host, expressing in vivo the heterologous polypeptide along with the EHV polypeptides. The polypeptides expressed in the inoculated host will then elicit an immune response against both EHV and the specific pathogen. If the heterologous polypeptide derived from the specific pathogen can stimulate a protective immune response, then the animal inoculated with an EHV mutant according to the invention will be immune to subsequent infection by that pathogen as well as to infection by EHV. Thus, a heterologous nucleic acid sequence incorporated into the region of the EHV genome according to the invention may be continuously expressed in vivo, providing a solid, safe and longlasting immunity to the equine pathogen.

An EHV mutant according to the invention containing and expressing one or more different heterologous polypeptides can serve as a monovalent or multivalent vaccine.

For the preparation of a live vaccine the EHV mutant according to the present invention can be grown on a cell culture of equine origin or on cells from other species. The viruses thus grown can be harvested by collecting the tissue cell culture fluids and/or cells. The live vaccine may be prepared in the form of a suspension or may be lyophilized.

In addition to an immunogenically effective amount of the EHV mutant the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F(R) or Marcol 52(R), saponins or vitamin-E solubilisate.

The useful dosage to be administered will vary depending on the age and weight of the animal, and mode of administration. A suitable dosage can range for example from $10^{3.0}$ to $10^{8.0}$ $TCID_{50}$ of the EHV mutant per horse.

An EHV mutant according to the invention can also be used to prepare an inactivated vaccine.

For administration to the animal, the EHV mutant according to the presentation can be given inter alia intranasally, intradermally, subcutaneously or intramuscularly.

EXAMPLE 1

Construction of the cosmid set for generating EHV-1 viruses

The SuperCos 1 cosmid vector kit was purchased from Stratagene (Catalog# 251301). This vector was further modified by adding extra restriction enzyme sites to it. A DNA linker was purchased from Pharmacia containing the following restriction sites: BamHI, I-SceI, PacI, AscI, EcoRV, PacI, AscI, I-SceI, and BamHI. The SuperCos 1 vector and the linkers were both cut with BamHI (New England Biolabs) according to the manufacturers instructions. The BamHI digested vector was dephosphorylazed with alkaline phosphatase (new England Biolabs) according the manufacturers instructions. The BamHI digested linker was then ligated into the SuperCos 1 vector by T4 DNA ligase (New England Biolabs) according to the manufacturers instructions. The resulting vector was then further used for cloning the EHV-1 inserts.

Viral DNA was obtained from the EHV-1 M8 strain, a pathogenic EHV-1 strain isolated from a horse with severe signs of an EHV-1 infection. This strain was incubated at an MOI of 1:1 on a confluent monolayer of Vero cells. After 4 days at 80% CPE cells, and supernatant were freeze thawed 3 times. To remove the cellular components the cells and supernatant were centrifuged for 30 min at 5000 rpm in a Sorrel superspeed centrifuge (RC-5C). The supernatant was then removed and centrifuged for two hours at 19.000 rpm in a Beckman Ultracentrifuge (L8-70). The pellets were resuspended in 1 ml of PBS. DNA extraction was done by adding EDTA and SDS to a final concentration of 10 mM and 2% respectively to lyse the virus.

This mixture was then extracted with phenol for at least 3 times according to standard techniques until no interface was seen any more. The DNA was then precipitated with 2 volumes of 100% ethanol at room temperature. After spinning at 12000 rpm for 10 min the ethanol was removed and the pellet washed with 70% ethanol. The pellet was then air dried and resuspended in water.

The EHV-1 DNA was sheared or digested to obtain the inserts needed for the cosmid set. Cosmids were constructed by digestion of the EHV-1 DNA with PacI (New England Biolabs). After phenol extraction of the M8 Pac-1 digests, the ends were filed in with T4 DNA polymerase (New England Biolabs) and then dephosphorylated with alkaline phosphatase (New England Biolabs) according the manufacturers instructions. The cosmid vector was digested with EcoRV (New England Biolabs) and the inserts were ligated into the vector with T4 DNA ligase (New England Biolabs). The ligation mix was packed in a packaging mix (Gigapack packaging extracts, Stratagene) according the manufacturers instructions. The packaged DNA was added to a fresh overnight culture of *E. coli* DH1 and placed for 1 hour at 37° C. The bacteria suspension was then spread onto agar plates containing ampicillin. All colonies were analyzed for their insertions by restriction enzyme analyses. For the construction of other cosmids the same procedure was followed only now the viral DNA was digested with AscI, AseI, RsrI, or NotI, all ends were then filled in with T4 DNA polymerase and the inserts ligated into the EcoRV site of the vector. To obtain a third generation of cosmids the viral DNA was sheared twice trough a 19 G needle, the ends were then filled in with T4 DNA polymerase and after phenol extraction and precipitation the inserts were cloned again into the EcoRV site of the cosmid vector. The vector with the inserts was then packed, put on bacteria and the colonies analyzed. From all colonies obtained the restriction maps were determined by multiple digestions. Then the location of the different clones were determined by comparing the restriction maps of the clones with the restriction map of EHV-1. All cosmids and their features generated by these methods are summarized in FIG. 1. Based on these data several cosmid sets were formed and tested for their ability to generate new viruses. With the cosmid set shown in Table 1, viable viruses could be regenerated. For the regeneration of viruses, the EHV-1 inserts were excised from the cosmids by a Sce-I (New England Biolabs) digestion. Then a confluent monolayer of BHK cells was transfected with 0.2 μg of each cosmid of the set by the calcium phosphate method. With this method more then 30 plaques harbouring viable virus were obtained per transfection.

TABLE 1

EHV-1 M8 cosmid set

| Cosmid | Insert Source | EHV-1 Insert Size | Left Terminus | Right Terminus | Genes | Overlap |
|---|---|---|---|---|---|---|
| 2D3 | pacI digest | 43 kbp | 1 | 42750 | start-24 | 5.4 kbp |
| 1A12 | shear | 36.3 kbp | 37337 | 73645 | 24–39 | 26.8 kbp |
| 1F4 | pacI digest | 43 kbp | 46810 | 89975 | 24–49 | 17.2 kbp |
| 2C12 | ascI digest | 44.1 kbp | 72760 | 116869 | 39–64 | 8.3 kbp |
| 2D9 | pacI digest | 41.6 kbp | 108640 | 150200 | 62-end | |

(Numbering derived from comparison with that of strain Ab4)

EXAMPLE 2

Generation of EHV-1 gene 15 mutants

Figure 2:
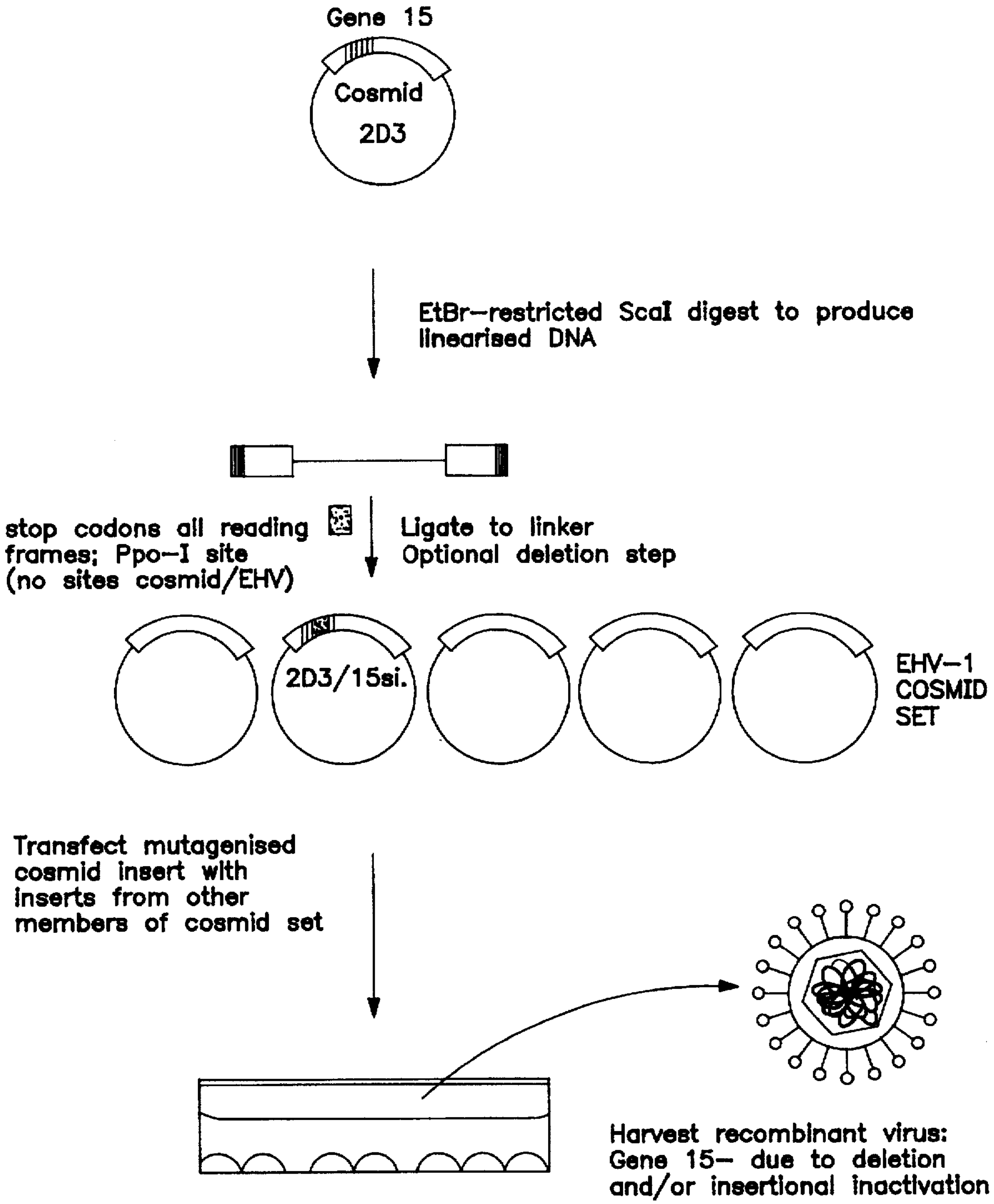
FIG. 2 shows the general strategy for the production of EHV-1 gene 15 mutants.
Figure 3A:
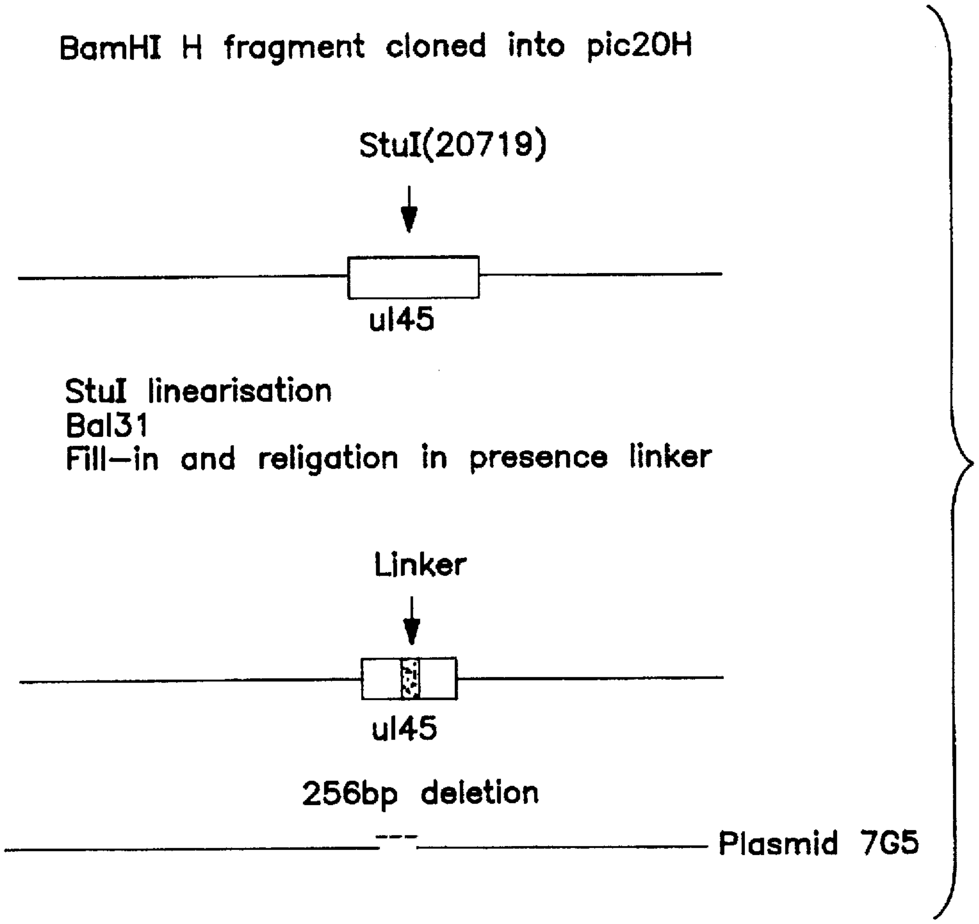
FIG. 3A shows the gene 15 plasmid deletion construct, 7G5.
Figure 3B:
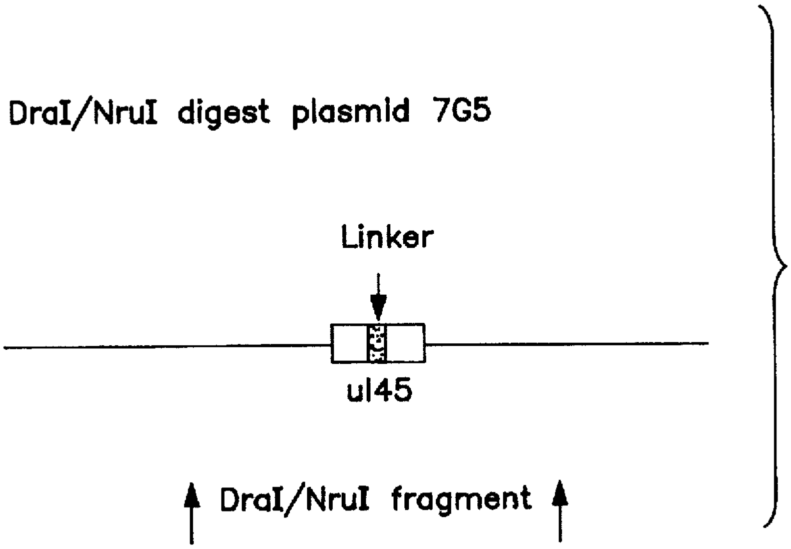
FIG. 3B shows the cloning of 600 bp fragment containing UL45 deletion/linker into SalI site pGEM-3Z to give plasmid UL45-E3.

To inactivate gene 15, cosmid 2D3 is digested with ScaI (New England Biolabs) in the presence of 100 μg/ml ethidium bromide. ScaI cuts 6 times within the cosmid 2D3, but by performing the digestion in the presence of ethidium bromide the production of full length linear cosmid molecules is favoured. Blunt end cosmids are generated by T4 DNA polymerase (New England Biolabs), these ends are then dephosphorylated with alkaline phosphatase. The 57 bp linker containing 3 stop codons in all reading frames and an I-PpoI recognitition sequence (SEQ ID NO: 5) is ligated into the linearized 2D3. All clones generated after transformation of *E. coli* DHI are analyzed by restriction enzyme analysis. The clones with a linker insertion in the gene 15 only, are isolated. Regeneration of the mutant virus is performed by replacing cosmid 2D3 with a cosmid having a linker insertion in gene 15 2D3/15si (FIG. 2 and Table 1) and performing the transformation as above. Regenerated viruses are plague purified 3 times and analyzed by restriction enzyme analysis.'

EXAMPLE 3

Generation of gene 15 Recombinant EHV-1.

1. Construction of gene 15 deletion/insertion mutant.

EHV-1 cosmid 2D3 was digested with BamHI. The resultant 7 kb fragment (19398–26260) containing the gene 15 homologue (20487–21146) was cloned into the BamHI site of pIC20H (Marsh, J. L., Erfle, M. and Wykes, E. J. 1984, Gene 32, 481–485). StuI was used to linearise this plasmid construct within gene 15 (at 20719). The linearised plasmid was then subjected to Bal 31 exonuclease digestion and after variable incubation periods, the plasmid was blunt-ended, ligated to the SEQ ID NO: 5 oligonucleotide and re-circularised to generate a plasmid with a linker insertion within the deleted portion of gene 15. This construct was named 7G5. The extent of the deletion and confirmation of insertion, was determined by restriction endonuclease mapping and sequencing using the CMA and CMB sites within the oligonucleotide shown in SEQ ID NO: 5. The deletion was delineated as nucleotides 20639 to 20894 inclusive. A second gene 15 deletion/insertion construct was produced, by DraI/NruI double digest of 7G5, generating a 600 base pair fragment containing gene 15 which was cloned into the SalI site of pGEM-3Z. This construct was termed gene 15-E3.

2. Cotransfection of 7G5 and gene 15-E3 with EHV-1 DNA.

6 μg of an EHV-1 genomic and cellular (Baby Hamster Kidney, BHK) DNA preparation and 2 μg of 7G5 or gene 15-E3 were transfected into monolayers of BHK or Swine Kidney (SK) cells on 8 cm diameter tissue culture plates, using the Stratagene calcium phosphate protocol. Following a 5 hour incubation with the DNA-phosphate precipitate, cells were "shocked" with 25% (v/v) DMSO in Hepes-buffered saline (pH 6.9) for 3 minutes (to boost transfection efficiency). After two washes in medium, cells were overlaid with 1.5% low melting-point agarose in MEM with 2% foetal calf serum and incubated at 37° C. Plaques were observed after 4–5 days culture. At this point the overlays were removed and stored at 4° C. The cell monolayers were adhered to nitrocellulose filters and cells disrupted (and DNA denatured) by a 5 minute incubation on Whatman paper soaked in 1.5M-sodium chloride/0.5M-sodium hydroxide. The alkali was neutralised with 1M-tris.Cl (pH 7.4)/1.5M-sodium chloride and two rinses with 2× SSC and the filters baked for two hours at 80° C in a vacuum oven. Filters were washed for 30 minutes at 70° C. with 1M-sodium chloride/0.1% (w/v) SDS to remove protein and cellular debris, followed by prehybridisation at 60° C. for 30 minutes in H-mix (10 mM-tris.Cl (pH 8.0) containing 1M-sodium chloride, 0.1% (w/v) SDS and 4× Denhardt's). $^{32}P$-endlabelled single strands of SEQ ID NO: 5 or the antisense strand were then added to the M-mix and filters hybridised overnight. Non-specific hybridisation signals were removed by a series of 15 minute washes at 65° C. with 2× SSC, 1× SSC and 0.5× SSC, all containing 0.1% (w/v) SDS. Filters were exposed to X-ray film for two days at −70° C.

3. Identification and Verification of Recombinant gene 15-EHV-1.

Using the location of plaques on the original plate, spots on the autoradiograph and the orientation (marked onto plates, overlays, filters and film) plugs of agarose were punched out from the overlay at potential recombinant plaques. These were vortexed with 0.5 ml medium to release virus and were used to infect further SK or BHK cells. The supernatants from these infections were used, in serial dilutions, to infect yet more SK or BHK cells, which were overlaid following virus adsorption, and then processed in an identical manner to that described above for the original cotransfections. After one or two rounds of plaque purification it was observed that the majority of plaques hybridised with the antisense strand of SEQ ID NO: 5. Consequently, four plaque purified viruses were picked and used to infect large flasks of BHK or SK cells. DNA was purified from these cells (a mix of viral and cellular DNA as used in the original cotransfection) and subjected to analysis by PCR and DNA sequencing (using CMA and CMB) to confirm the presence of the deletion/insertion gene 15 mutant in the vital genome.

---

We claim:

1. An isolated nucleic acid molecule comprising gene 15 of EHV and flanking sequence thereof, wherein the gene 15 comprises a mutation which prevents production of a functional gene 15 protein.

2. A recombinant DNA molecule comprising a nucleic acid molecule according to claim 1.

3. A host cell transfected with the recombinant DNA molecule according to claim 2.

4. An Equine herpesvirus (EHV) mutant comprising a mutation in gene 15, where in said EHV mutant fails to produce a functional gene 15 protein.

5. The EHV mutant according to claim 4, wherein the EHV mutant is an EHV-1 having a mutation in gene 15, wherein non-mutated gene 15 encodes a polypeptide having an amine acid sequence shown in SEQ ID NO:2.

6. The EHV mutant according to claim 4, wherein the EHV mutant is an EHV-4 having a mutation in gene 15, wherein non-mutated gene 15 encodes a polypeptide having an amino acid sequence shown in SEQ ID NO:4.

7. The EHV mutant according to claim 4, wherein the mutation is an insertion and/or deletion.

8. The EHV mutant according to claim 7, wherein the mutation is an insertion comprising a heterologous gene encoding an antigen of an equine pathogen.

9. A process for the preparation of an EHV mutant according to claim 4, comprising transfecting a cell culture with the recombinant DNA molecule according to claim 7 and EHV genomic DNA.

10. A cell culture infected with an EHV mutant according to claim 4.

11. An immunogenic composition comprising EHV mutant according to claim 4 and a pharmaceutically acceptable carrier or diluent.

12. An immunogenic composition comprising an EHV mutant according to claim 5 and a pharmaceutically acceptable carrier or diluent.

13. An immunogenic composition comprising an EHV mutant according to claim 6 and a pharmaceutically acceptable carrier or diluent.

14. A method for the immunization of a horse against equine herpesvirus comprising administering to the horse a composition according to claim 12.

15. A method for the immunization of a horse, comprising administering to the horse an immunogenic composition according to claim 11.

16. A method for the immunization of a horse against equine herpesvirus comprising administering to the horse a composition according to claim 13.

* * * * *

UNITED STATES PATENT AND TRADEMARK OFFICE

CERTIFICATE OF CORRECTION

PATENT NO. : 5,674,499

DATED : October 7, 1997

INVENTOR(S) : Willemse et al.

It is certified that error appears in the above-indentified patent and that said Letters Patent is hereby corrected as shown below:

Please correct column 17, line 2 of Claim 1 by changing "sequence" to -- sequences --

Signed and Sealed this

Twenty-third Day of December, 1997

Attest:

BRUCE LEHMAN

Attesting Officer

*Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 683 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Equine Herpes Virus 1
( B ) STRAIN: Ab4

( i x ) FEATURE:
( A ) NAME/KEY: CDS
( B ) LOCATION: 1..683

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GCA | GGA | GAC | CCA | ACA | GCT | GCG | ATG | GAA | GAT | TAT | AAA | TTA | CTA | CAG | 48 |
| Met | Ala | Gly | Asp | Pro | Thr | Ala | Ala | Met | Glu | Asp | Tyr | Lys | Leu | Leu | Gln | |
| 1 | | | | 5 | | | | | 10 | | | | | 15 | | |
| CTG | GAA | ACC | GCC | ACC | GTC | GAT | GCT | CAG | GCT | CCC | CCC | TTA | CCA | ACG | AAA | 96 |
| Leu | Glu | Thr | Ala | Thr | Val | Asp | Ala | Gln | Ala | Pro | Pro | Leu | Pro | Thr | Lys | |
| | | | 20 | | | | | 25 | | | | | 30 | | | |
| ACC | GTT | CCG | GTG | TTT | GCG | CCC | CCG | CTG | TCA | ACC | CCC | CCT | CAA | CCC | AAC | 144 |
| Thr | Val | Pro | Val | Phe | Ala | Pro | Pro | Leu | Ser | Thr | Pro | Pro | Gln | Pro | Asn | |
| | | 35 | | | | | 40 | | | | | 45 | | | | |
| GAG | CTT | GTT | TAT | ACA | AAG | CGA | CGC | AGA | ACA | AAG | CGC | AAA | GCA | AAA | TGC | 192 |
| Glu | Leu | Val | Tyr | Thr | Lys | Arg | Arg | Arg | Thr | Lys | Arg | Lys | Ala | Lys | Cys | |
| | 50 | | | | | 55 | | | | | 60 | | | | | |
| CGC | TGC | CTT | TTT | TTT | ACG | ATG | GGC | ATG | TTT | GCG | CTG | GGG | GTT | TTG | ATG | 240 |
| Arg | Cys | Leu | Phe | Phe | Thr | Met | Gly | Met | Phe | Ala | Leu | Gly | Val | Leu | Met | |
| 65 | | | | | 70 | | | | | 75 | | | | | 80 | |
| ACA | ACC | GCC | ATT | CTG | GTG | TCC | ACC | TTC | ATA | TTA | ACA | GTA | CCT | ATT | GGC | 288 |
| Thr | Thr | Ala | Ile | Leu | Val | Ser | Thr | Phe | Ile | Leu | Thr | Val | Pro | Ile | Gly | |
| | | | | 85 | | | | | 90 | | | | | 95 | | |
| GCG | CTA | CGC | ACG | GCA | CCG | TGT | CCC | GCA | GAG | ACT | TTT | GGT | CTG | GGG | GAC | 336 |
| Ala | Leu | Arg | Thr | Ala | Pro | Cys | Pro | Ala | Glu | Thr | Phe | Gly | Leu | Gly | Asp | |
| | | | 100 | | | | | 105 | | | | | 110 | | | |
| GAG | TGT | GTT | CGC | CCG | GTG | TTG | CTG | AAC | GCA | TCA | TCC | AAC | ACA | CGC | AAC | 384 |
| Glu | Cys | Val | Arg | Pro | Val | Leu | Leu | Asn | Ala | Ser | Ser | Asn | Thr | Arg | Asn | |
| | | 115 | | | | | 120 | | | | | 125 | | | | |
| ATC | AGC | GGG | GTG | GGG | GCA | GTA | TGC | GAA | GAG | TAC | TCA | GAG | ATG | GCG | GCT | 432 |
| Ile | Ser | Gly | Val | Gly | Ala | Val | Cys | Glu | Glu | Tyr | Ser | Glu | Met | Ala | Ala | |
| | 130 | | | | | 135 | | | | | 140 | | | | | |
| TCT | AAT | GGC | ACT | GCA | GGC | CTA | ATA | ATG | AGT | CTG | CTG | GAC | TGC | CTC | AAC | 480 |
| Ser | Asn | Gly | Thr | Ala | Gly | Leu | Ile | Met | Ser | Leu | Leu | Asp | Cys | Leu | Asn | |
| 145 | | | | | 150 | | | | | 155 | | | | | 160 | |
| GTG | GGA | GAT | AGC | GAA | TCC | GTT | ATG | AAT | AAG | CTC | AAC | CTC | GAT | GAT | ACT | 528 |
| Val | Gly | Asp | Ser | Glu | Ser | Val | Met | Asn | Lys | Leu | Asn | Leu | Asp | Asp | Thr | |
| | | | | 165 | | | | | 170 | | | | | 175 | | |
| CAG | CTG | GCC | TAC | TGC | AAC | GTA | CCG | AGC | TTC | GCA | GAA | TGC | TAC | ACC | AAG | 576 |
| Gln | Leu | Ala | Tyr | Cys | Asn | Val | Pro | Ser | Phe | Ala | Glu | Cys | Tyr | Thr | Lys | |

-continued 180 185 190

GGG TTT GGT GTG TGC TAT GCA GCC CGC CCA CTC AGC CCG CTT GGA GAG 624
Gly Phe Gly Val Cys Tyr Ala Ala Arg Pro Leu Ser Pro Leu Gly Glu
195 200 205

CTG ATC TAC AAG GCC CGC CAA GCG CTT CGT CTG GAC CAC ATC ATA CCG 672
Leu Ile Tyr Lys Ala Arg Gln Ala Leu Arg Leu Asp His Ile Ile Pro
210 215 220

TTT CCC CGG TA 683
Phe Pro Arg
225

( 2 ) INFORMATION FOR SEQ ID NO:2:

( i ) SEQUENCE CHARACTERISTICS:
( A ) LENGTH: 227 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ala Gly Asp Pro Thr Ala Ala Met Glu Asp Tyr Lys Leu Leu Gln
1 5 10 15

Leu Glu Thr Ala Thr Val Asp Ala Gln Ala Pro Pro Leu Pro Thr Lys
20 25 30

Thr Val Pro Val Phe Ala Pro Pro Leu Ser Thr Pro Pro Gln Pro Asn
35 40 45

Glu Leu Val Tyr Thr Lys Arg Arg Arg Thr Lys Arg Lys Ala Lys Cys
50 55 60

Arg Cys Leu Phe Phe Thr Met Gly Met Phe Ala Leu Gly Val Leu Met
65 70 75 80

Thr Thr Ala Ile Leu Val Ser Thr Phe Ile Leu Thr Val Pro Ile Gly
85 90 95

Ala Leu Arg Thr Ala Pro Cys Pro Ala Glu Thr Phe Gly Leu Gly Asp
100 105 110

Glu Cys Val Arg Pro Val Leu Leu Asn Ala Ser Ser Asn Thr Arg Asn
115 120 125

Ile Ser Gly Val Gly Ala Val Cys Glu Glu Tyr Ser Glu Met Ala Ala
130 135 140

Ser Asn Gly Thr Ala Gly Leu Ile Met Ser Leu Leu Asp Cys Leu Asn
145 150 155 160

Val Gly Asp Ser Glu Ser Val Met Asn Lys Leu Asn Leu Asp Asp Thr
165 170 175

Gln Leu Ala Tyr Cys Asn Val Pro Ser Phe Ala Glu Cys Tyr Thr Lys
180 185 190

Gly Phe Gly Val Cys Tyr Ala Ala Arg Pro Leu Ser Pro Leu Gly Glu
195 200 205

Leu Ile Tyr Lys Ala Arg Gln Ala Leu Arg Leu Asp His Ile Ile Pro
210 215 220

Phe Pro Arg
225

( 2 ) INFORMATION FOR SEQ ID NO:3:

( i ) SEQUENCE CHARACTERISTICS:
( A ) LENGTH: 680 base pairs
( B ) TYPE: nucleic acid
( C ) STRANDEDNESS: double
( D ) TOPOLOGY: linear -continued ( i i ) MOLECULE TYPE: DNA (genomic)

( v i ) ORIGINAL SOURCE:
( A ) ORGANISM: Equine Herpes Virus 4
( B ) STRAIN: 1942

( i x ) FEATURE:
( A ) NAME/KEY: CDS
( B ) LOCATION: 1..680

( x i ) SEQUENCE DESCRIPTION: SEQ ID NO:3:

ATG TCT GGA GAC CCA ACA GCT TCG CTA AAA GAT TAT CAA TTA CTG GAG 48
Met Ser Gly Asp Pro Thr Ala Ser Leu Lys Asp Tyr Gln Leu Leu Glu
1 5 10 15

CTT GAT ACA GCT GCC GGT AAT GAT CAA GCT CCC CAA CTA CCT ACA AAG 96
Leu Asp Thr Ala Ala Gly Asn Asp Gln Ala Pro Gln Leu Pro Thr Lys
20 25 30

ACT GTT TTG GGG TTT ACA CCA CCG CTG CCG ACT CTA CCC CAA CCA ACC 144
Thr Val Leu Gly Phe Thr Pro Pro Leu Pro Thr Leu Pro Gln Pro Thr
35 40 45

GAA CTC GTT TAT ACA AAA CGG CGC CGA CCA AAA CGC AGA TCT AGA TGC 192
Glu Leu Val Tyr Thr Lys Arg Arg Arg Pro Lys Arg Arg Ser Arg Cys
50 55 60

CGC TGC CTC TGT TTT ACG ATG GGT ATG TTT GCG ATG GGG GTT CTA ATG 240
Arg Cys Leu Cys Phe Thr Met Gly Met Phe Ala Met Gly Val Leu Met
65 70 75 80

ACC ACC ACA CTT TTG GTG TCT ACC TTT GTC CTA ACA GTA CCC ATG GTC 288
Thr Thr Thr Leu Leu Val Ser Thr Phe Val Leu Thr Val Pro Met Val
85 90 95

GCG CTA CGC ACA GCA CCA TGT CCA GCG CAA ACC TTT GGT CTG GGT GAC 336
Ala Leu Arg Thr Ala Pro Cys Pro Ala Gln Thr Phe Gly Leu Gly Asp
100 105 110

GAG TGT GTA CGC CCC GTG TCG CTA GAC GCT TAC AAC AGC AGC AAC TCT 384
Glu Cys Val Arg Pro Val Ser Leu Asp Ala Tyr Asn Ser Ser Asn Ser
115 120 125

AGC GAA ATA GGG GCT GTA TGT GGA GCA TAT TCT GAG ATG CCA GCC CCG 432
Ser Glu Ile Gly Ala Val Cys Gly Ala Tyr Ser Glu Met Pro Ala Pro
130 135 140

GAT AAC ACT ACT GTC CTG ATA ATG AAC CTT CTG GAC TGC CTA AAC ATT 480
Asp Asn Thr Thr Val Leu Ile Met Asn Leu Leu Asp Cys Leu Asn Ile
145 150 155 160

GGC ATC AAC GAA TCG GCT GGA GAA AAA CTA AAT CTG ACG GAC ACA CCA 528
Gly Ile Asn Glu Ser Ala Gly Glu Lys Leu Asn Leu Thr Asp Thr Pro
165 170 175

CTT GCA AAC TGT AAC TTT TCA CAA AAC TCG GTA TGC TCC AGA AAA CGC 576
Leu Ala Asn Cys Asn Phe Ser Gln Asn Ser Val Cys Ser Arg Lys Arg
180 185 190

GTT GGT GTG TGC TAC GCC GCC CGC CCA CTC AGC CCA CTT GGA GAG TTG 624
Val Gly Val Cys Tyr Ala Ala Arg Pro Leu Ser Pro Leu Gly Glu Leu
195 200 205

ATT TAC AAG GCC CGC CAG GCG CTT CGG CTT GAC CAC ATT CTT CCA TTT 672
Ile Tyr Lys Ala Arg Gln Ala Leu Arg Leu Asp His Ile Leu Pro Phe
210 215 220

TTG CAG TA 680
Leu Gln
225

( 2 ) INFORMATION FOR SEQ ID NO:4:

( i ) SEQUENCE CHARACTERISTICS:
( A ) LENGTH: 226 amino acids
( B ) TYPE: amino acid
( D ) TOPOLOGY: linear -continued ( i i ) MOLECULE TYPE: protein ( x i ) SEQUENCE DESCRIPTION: SEQ ID NO:4:

Met Ser Gly Asp Pro Thr Ala Ser Leu Lys Asp Tyr Gln Leu Leu Glu
1 5 10 15

Leu Asp Thr Ala Ala Gly Asn Asp Gln Ala Pro Gln Leu Pro Thr Lys
20 25 30

Thr Val Leu Gly Phe Thr Pro Pro Leu Pro Thr Leu Pro Gln Pro Thr
35 40 45

Glu Leu Val Tyr Thr Lys Arg Arg Arg Pro Lys Arg Arg Ser Arg Cys
50 55 60

Arg Cys Leu Cys Phe Thr Met Gly Met Phe Ala Met Gly Val Leu Met
65 70 75 80

Thr Thr Thr Leu Leu Val Ser Thr Phe Val Leu Thr Val Pro Met Val
85 90 95

Ala Leu Arg Thr Ala Pro Cys Pro Ala Gln Thr Phe Gly Leu Gly Asp
100 105 110

Glu Cys Val Arg Pro Val Ser Leu Asp Ala Tyr Asn Ser Ser Asn Ser
115 120 125

Ser Glu Ile Gly Ala Val Cys Gly Ala Tyr Ser Glu Met Pro Ala Pro
130 135 140

Asp Asn Thr Thr Val Leu Ile Met Asn Leu Leu Asp Cys Leu Asn Ile
145 150 155 160

Gly Ile Asn Glu Ser Ala Gly Glu Lys Leu Asn Leu Thr Asp Thr Pro
165 170 175

Leu Ala Asn Cys Asn Phe Ser Gln Asn Ser Val Cys Ser Arg Lys Arg
180 185 190

Val Gly Val Cys Tyr Ala Ala Arg Pro Leu Ser Pro Leu Gly Glu Leu
195 200 205

Ile Tyr Lys Ala Arg Gln Ala Leu Arg Leu Asp His Ile Leu Pro Phe
210 215 220

Leu Gln
225

( 2 ) INFORMATION FOR SEQ ID NO:5:

( i ) SEQUENCE CHARACTERISTICS:
( A ) LENGTH: 57 base pairs
( B ) TYPE: nucleic acid
( C ) STRANDEDNESS: double
( D ) TOPOLOGY: linear ( i x ) FEATURE:
( A ) NAME/KEY: -
( B ) LOCATION: 1..57
( C ) OTHER INFORMATION: /label=synthetic linker ( x i ) SEQUENCE DESCRIPTION: SEQ ID NO:5:

ATCTGGATCT AGCTGATTGA CTCTCTTAAG GTAGCTAGTT ACTCATGAAT TCCTGAT 57